United States Patent [19]

Lee et al.

[11] Patent Number: 4,628,267
[45] Date of Patent: Dec. 9, 1986

[54] MEASURING OF ELECTRICAL CHANGES INDUCED BY IN SITU COMBUSTION THROUGH FLOW-THROUGH ELECTRODES IN A LABORATORY SAMPLE OF CORE MATERIAL

[75] Inventors: David O. Lee; Paul C. Montoya; James R. Wayland, Jr., all of Albuquerque, N. Mex.

[73] Assignee: The United States of America as represented by the United States Department of Energy, Washington, D.C.

[21] Appl. No.: 485,154

[22] Filed: Apr. 15, 1983

[51] Int. Cl.$^4$ .............................................. G01V 3/02
[52] U.S. Cl. .................................. 324/376; 324/65 R
[58] Field of Search ...................... 324/376, 377, 71.1, 324/448, 446, 323, 65 P, 61 R, 323, 65 R

[56] References Cited

U.S. PATENT DOCUMENTS

| | | | |
|---|---|---|---|
| 2,802,172 | 8/1957 | Mueller et al. | 324/376 |
| 2,807,956 | 10/1957 | Doble | 324/61 R |
| 2,973,811 | 3/1961 | Rogers | 324/323 X |
| 3,262,106 | 7/1966 | Crawford et al. | 324/439 X |
| 3,283,243 | 11/1966 | Richardson et al. | 324/65 P |
| 3,302,101 | 1/1967 | Glanville | 324/376 |
| 3,376,501 | 4/1968 | Peranio | 324/65 P |
| 3,412,325 | 11/1968 | Soderling | 324/65 P |
| 3,424,977 | 1/1969 | Krobath | 324/61 R |
| 3,617,868 | 11/1971 | Beitel et al. | 324/376 |
| 3,772,589 | 11/1973 | Scholberg | 324/375 X |
| 3,982,177 | 9/1976 | Walker et al. | 324/376 |
| 4,210,867 | 7/1980 | Ginsburgh et al. | 324/323 |
| 4,210,868 | 7/1980 | Ginsburgh et al. | 324/323 |

OTHER PUBLICATIONS

Hyndman et al., "The Measurement of Marine . . . In Situ Thermal Conductivity", Marine Geophysical Researches, vol. 4, No. 2, Dec. 1979, pp. 181-205.
Neuman, "Log Core Measurement of Oil in Place San Joaquin Valley", Journal of Petroleum Technology, Aug. 1980, pp. 1309-1315.
SAND82-0874, Wayland et al, "Measurement of Resistivity Changes Induced by In-Situ Combustion," Jul. 1982.
Society of Petroleum Engineers Paper SPE 11051, Lee et al, "Measurement of Formation Resistivity Changes Induced by In-Situ Combustion", Sep. 26-29, 1982.

*Primary Examiner*—Reinhard J. Eisenzopf
*Assistant Examiner*—Warren S. Edmonds
*Attorney, Agent, or Firm*—George H. Libman; Albert Sopp; Judson R. Hightower

[57] ABSTRACT

Method and apparatus are provided for obtaining accurate dynamic measurements for passage of phase fronts through a core sample in a test fixture. Flow-through grid structures are provided for electrodes to permit data to be obtained before, during and after passage of a front therethrough. Such electrodes are incorporated in a test apparatus for obtaining electrical characteristics of the core sample. With the inventive structure a method is provided for measurement of instabilities in a phase front progressing through the medium. Availability of accurate dynamic data representing parameters descriptive of material characteristics before, during and after passage of a front provides a more efficient method for enhanced recovery of oil using a fire flood technique.

11 Claims, 12 Drawing Figures

U.S. Patent  Dec. 9, 1986  Sheet 1 of 3  4,628,267

MEASURING OF ELECTRICAL CHANGES INDUCED BY IN SITU COMBUSTION THROUGH FLOW-THROUGH ELECTRODES IN A LABORATORY SAMPLE OF CORE MATERIAL

The U.S. government has rights in this invention pursuant to contract No. DE-AC04-76DP00789 between the U.S. Department of Energy and Western Electric Company.

BACKGROUND OF THE INVENTION

This invention relates to method and apparatus for measuring electrical parameters of geological core samples, and more specifically to nondestructive test electrodes for use in obtaining the descriptive data, to a test apparatus incorporating the test electrodes, and to a method to obtain data indicative of frontal instabilities associated with the movement of immiscible substances through porous media by measuring changes in electrical characteristics of the core sample.

A number of processes are known for enhanced recovery of oil from underground reservoirs. such recovery processes typically involve an injection of a specified material into the reservoir at an injection well and recovery of the oil in a producing well. The various processes utilized in such enhanced recovery of oil include water flooding, surfactant flooding, gas injection (e.g., carbon dioxide) and application of heat, for example. The heat applied to the stored hydrocarbons may be derived from combustion of a portion of the in-place oil (in situ combustion) or, alternatively, may be externally generated and provided to the reservoir by a heat carrier such as steam or hot water injected into the underground formation.

In each of the above processes, various phase fronts are displaced within the underground reservoir. Such phase fronts include, for example, interfaces between the injected materials and the underground hydrocarbons, interfaces between various combustion products of the underground hydrocarbons, temperature fronts and flame fronts.

In order to recover maximal quantities of oil it is desirable to know the displacement of the various underground fronts and the direction of travel thereof. Such knowledge enables the drilling of production wells at appropriate sites, as opposed to using arbitrary geometrical patterns for injection and production wells. Additionally, information pertinent to the displacement of the various fronts permits drilling of two types of additional wells to increase oil recovery. Injection wells may be drilled for injection of controlling substances to direct oil towards production wells. Additionally, new production wells may be drilled at the location of the fronts or at a determined forthcoming location thereof.

Accordingly, the prior art has developed techniques for analysis of the response of reconstituted geological core samples to various ones of the injection and flooding processes. Laboratory equipment has been developed, for example, to provide physical and chemical analysis of various combustion products of a core sample, simulating an in situ or underground combustion recovery process, as described in "Secondary and Tertiary Oil Recovery Processes", Interstate Oil Compact Commission, Oklahoma City, Okla., September 1974 at pages 100-101.

A different combustion tube system is described in Harding et al., "Adiabatic Combustion Tube Evaluation of In Situ Processes for Oil Sand", 26th Canadian Chemical Engineering Conference, Toronto, Canada (October 1976) and in Moore et al., "Observed In Situ Combustion Phenomena", preprint (1981). The described structure may be used to measure electrical characteristics of a reconstituted core sample subject to conditions simulating in situ combustion, water flood, steam flood, chemical flood, or any process where an agent is injected to improve recovery. The electrical characteristics of the sample, and the changes therein, are useful in determining the progress of the various fronts associated with enhanced oil recovery processes.

For example, it is known that substantial changes in resistivity occur in the reservoir materials as a consequence of passage of the various fronts therethrough. Such data may be detected in the field by electromagnetic induction geophysical prospecting techniques, such as the controlled source audio frequency magnetotelluric process described in Ostrander, "CSAMT—Application and Advantage", preprint of paper presented at 87th Annual Northwest Mining Association Convention, Spokane, Wash., Dec. 4, 1981, or the method described in Ginsburgh et al., U.S. Pat. No. 4,210,868. The interpretation of the field data requires knowledge of changes in the electrical characteristics of the specific formation subject to the enhanced recovery process.

There is thus a need in the prior art to provide laboratory equipment for providing accurate data representative of a simulated in situ combustion (or other enhanced oil recovery) process before, during and after the passage of a phase front therein.

Further, in order accurately to interpret prospecting data during an enhanced recovery process, it is necessary to be able to analyze frontal instabilities dynamically in the laboratory. The prior laboratory test equipment, subject to destruction and corrosion in response to various phases of the recovery process, cannot provide accurate data representative of frontal instabilities, temporary aberrations or similar data. There is thus a further need in the prior art for a method and apparatus for dynamic measurement of such frontal instabilities.

SUMMARY OF THE INVENTION

It is accordingly an object of the present invention to provide a test electrode permitting non-destructive passage of a phase front therethrough.

It is another object of the invention to provide a method for producing a test electrode permitting non-destructive passage of a phase front therethrough.

It is still a further object of the invention to provide test apparatus for obtaining electrical parameter data representative of a core of material including test electrodes which permit nondestructive passage of a phase front therethrough and which provide accurate output signals throughout the passage of the phase front.

Yet a further object of the invention is the provision of a method for measurement of instabilities in a phase front progressing through a medium.

It is still a more specific object of the invention to provide flow-through non-destructive electrodes for measurement of instabilities by measurement of changes in electrical parameters representative of progress of a phase front therebetween.

It is yet another object of the invention to provide capacitor electrodes in a test apparatus for measurement of capacitance changes therebetween representative of areas of instabilities in a phase front.

Additional objects, advantages and other novel features of the invention will be set forth in part in the description which follows and in part will become more apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purpose of the present invention as described herein, an improved test electrode is provided for use in obtaining electrical test data descriptive of a geological core sample. The test electrode includes a grid structure for enabling non-destructive passage of a phase front therethrough and for providing output electrical signals. The electrode further includes a connector for providing external connections to the grid.

Preferably, the grid is formed of a pattern of wires surrounded by an outer support and having a connector thereto. In one example, the grid may include a plurality of concentric circles and radial connectors. Other configurations may also be used, such as a rectangular pattern. The connector may comprise an outwardly extending tab. Moreover, the connector to the grid electrode may include sheathed stainless steel thermocouple wires having two ends thereof spot welded together, thereby providing electrical contact and enabling measurement of temperatures at the electrode. Preferably, to reduce resistance to (and disruption of) front passage, thus to avoid the introduction of additional instabilities, the wires forming the electrode grid occupy no more than approximately 5% of the area of the passing front.

More specifically, the invention includes a method for producing the grid electrode by the steps of photoetching a grid pattern on a conductive surface, producing a grid from the etching by chemical milling, plating the resulting grid with a protective material, attaching connecting sheathed electrode wire to the grid and sealing the sheathing of the connecting electrode wire.

In a further aspect of the invention, a test apparatus is provided for obtaining electrical parameter data for a core of material. The test apparatus includes a plurality of test electrodes and a housing for the electrodes and sections of the core material disposed between the electrodes. The electrodes include structural features to permit non-destructive passage of a phase front therethrough and to provide accurate electrical output signals throughout the passage of the phase front. Preferably, the test electrodes include the described grid structure, and the housing includes a plurality of zones disposed along the outer surface thereof. Where necessary, heaters may be placed along the tube.

In a further aspect of the invention, there is provided a method for measurement of instabilities of a phase front passing through a medium in a combustion tube, including the step of providing a number of flow-through electrodes in the medium. The electrical parameters between several of the electrodes are measured and changes in the measured parameters, representative of instabilities in phase displacement, are determined.

The measured electrical parameter may be resistance or capacitance, for example, changes therein being used to calculate the area covered by the phase front instabilities. Other electrical parameters may also be used. Additionally, the frontal displacement velocity as well as the velocity of instabilities (fingers) may be calculated as a function of the electrical parameter changes.

In a more specific aspect of the invention, there is provided an improved method for enhanced oil recovery (EOR) in which a reconstructed core sample is combined with a plurality of flow-through electrodes in a test fixture. Electrical characteristics of the sample, obtained before, during, and after passage of a flame (or any other) front therethrough, are used in combination with in situ measurements obtained during a recovery operation. Preferably, the area of fingers of the front is obtained as a function of the sample capacitance between the electrodes before, during and after passage of the front therethrough by performing a numerical computation on the measured capacitance.

Still other objects of the present invention will become readily apparent to those skilled in this art from the following description wherein there is shown and described a preferred embodiment of the invention, simply by way of illustration of one of the modes best suited to carry out the invention. As will be realized, the invention is capable of other, different embodiments, and its several details are capable of modifications in various obvious aspects, all without departing from the invention. Accordingly, the drawings and descriptions will be regarded as illustrative in nature and not as restrictive.

BRIEF DESCRIPTION OF THE DRAWINGS

The accompanying drawings, incorporated in and forming a part of the specification, illustrate several aspects of the present invention and, together with the description, serve to explain the principles thereof. In the drawings.

DETAILED DESCRIPTION OF THE INVENTION

Figure 1:
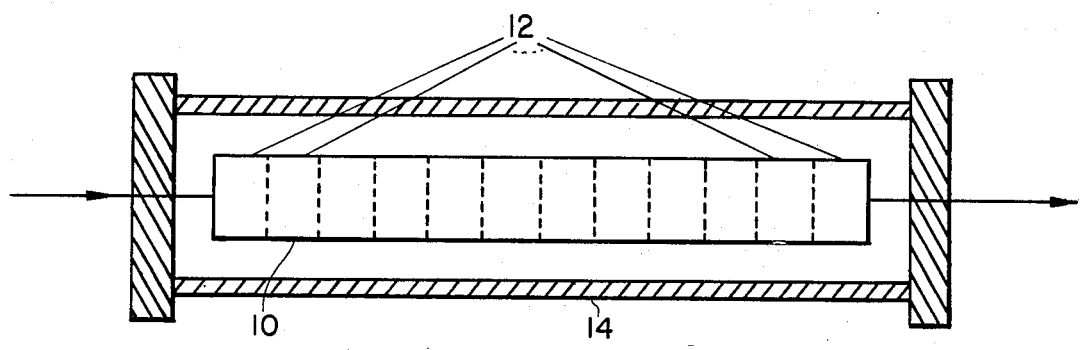
FIG. 1 illustrates a test fixture of the prior art as usable for the present invention.

Reference is first made to FIG. 1, showing a test fixture 10 utilized in the prior art for obtaining data representative of a core sample subject to laboratory experiments recreating enhanced oil recovery situations which include, for example, passages of thermal fronts.

Such a test fixture is normally constructed from thin walled metal tubing, e.g. 1.85 A meter length, 10.20 cm diameter, type 600 Inconel tubing of 1.067 mm wall thickness. The tube may have a plurality of heaters 12 on its outer surface, dividing the tube into plural zones. At each junction between the heating panels a thermocouple (not shown) is mounted on the inside tube wall and another thermocouple (not shown) is extended into the centerline of the core in the tube. Apart from the tube structure, automatic temperature controllers are used to control the power input to the individual heaters so that a near zero radial temperature gradient is maintained between the centerline and wall thermocouples. If the tube were to be run in a true adiabatic mode this temperature gradient would be zero. In actual practice a gradient of about 10° C. is maintained to ensure that the heaters do not drive the thermal front.

To help control the heat transfer and allow operation at high pressures, the tube is mounted in an insulated pressure vessel 14. The vessel is pressurized (with helium, for example) to balance the pressure in the combustion tube. Thus, in situ conditions can be simulated. Pressure sampling ports are provided at alternate sets of thermocouples. The tube acts as a core holder. The core is made from material taken from the formation under study or reconstituted from representative sand, clay, etc. The individual components of the test formation core are extracted from the original core and processed (ground up, analyzed and reconstituted) to provide sand (and fines), bitumen and reservoir water. This process is needed to ensure a homogeneous core. The resulting products are then used to make a reconstituted core in the tube. Effluent from the tube is passed through a high pressure separator to allow for sampling of the liquid and gaseous phases. The produced gas is analyzed using a gas chromatograph and the liquid phase is collected for further analysis.

It is possible to utilize a test fixture as hereinabove described as a screening tool for various surfactants and foams to be injected into the underground reservoir during enhanced recovery processes. During such processes, mobility control agents, such as surfactants and foams, may be injected to the underground reservoir. Surfactants, for example, may be injected to lessen surface tension and to direct the moving oil phase in a desired direction. Foam may be injected as a blocking agent for the moving phase fronts. The effectiveness of the particular control agents may be tested in a laboratory combustion tube by observation of various instabilities resulting from the injection of the agents. Additionally, measurements of resistivity, capacitance and other electrical parameters of the core provide significant information descriptive of passage of a front through the core medium. Such measurements are useful in detecting and mapping thermal and other fronts associated with enhanced oil recovery processes applied to an oil bearing formation. The experimental results obtained with the use of a combustion tube aid in interpretation of electromagnetic data obtained as a phase front passes through the reservoir materials in situ.

Typical laboratory test results provide data pertaining to temperatures and pressures of the core sample and of the fluids produced during the test. These data are useful in interpreting field test data which may be obtained by known methods of electromagnetic induction geophysical prospecting techniques.

Figure 2:
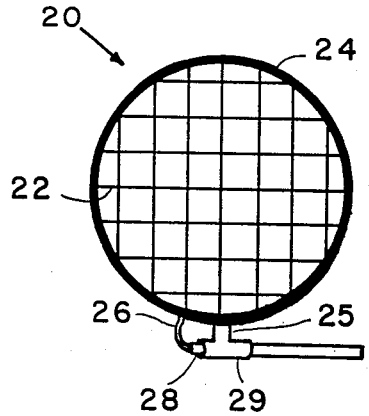
FIG. 2 shows the inventive test electrode.

In order to obtain more accurate interpretations of field data, the laboratory test results should be descriptive of the core material throughout all phases of the enhanced oil recovery technique. Reference is now made to FIG. 2, showing an example of the inventive test electrode usable in a structure such as shown in FIG. 1 to obtain accurate electrical measurements before, during, and after passage of a front therethrough. As shown in the figure, the inventive electrode 20 includes a computer generated rectangular grid pattern 22 of 0.51 mm wires on a 6 mm spacing surrounded by a 50 mm outer annulus 24 of 3 mm width. A small tab 25 extends from the outer annulus 24.

The computer generated pattern is then photoetched on 0.13 mm thick 304 stainless steel or other suitable material. The resulting electrodes are plated with Au by standard techniques. Electrical connection to the electrodes may be made with 2.18 mm chromel/alumel, stainless steel sheath thermocouple wire 26 (which may or may not also be used as temperature sensors), or other suitable electrical wire. Preferably, both ends of the thermocouple wire are spot welded together if not used as temperature sensors. The end of the thermocouple wires is spot welded to the electrode. The sheath is sealed at 28 with a glass ceramic to guard against penetration of moisture or corrosive agents into the thermocouple and shorting the wires to the sheath.

To perform the glassing operation and attach the electrical leads to the electrode grid, the sheath around the thermocouple wire 26 is stripped back, leaving the wire exposed. The ends of the thermocouple wires are then welded together. After welding, the wires and approximately 5 cm of the sheath are cleaned by immersion in a beaker of alcohol and placement of the immersed wires in an ultrasonic cleaner for two minutes. The wires are then placed under a heat lamp for complete drying. An insulator is inserted between the thermocouple sheath and a tubular sleeve 29 which is welded to the tab 25 on the electrode. The glass ceramic preform is preferably placed in equal lengths over the thermocouple wires and the sheath. A quartz tube is preferably placed over the wire and the sheath in the areas to be glassed to prevent the thermocouple wires from being burned when a gas and oxygen torch is used to flow the glass ceramic. Upon heating, the glass ceramic flows around the wire and sheath to prevent shorting problems.

Emplacement of the grids requires careful handling and new techniques to ensure that accurate spacing and orientation are maintained throughout the tube. The spacing is established using prefabricated disks of core material. The disks are made in a mold. A solution (50% distilled water and 50% methyl alcohol, for example) is mixed with the formation sand, placed in the mold and then dried under pressure. The resulting disk is relatively strong and stable. A check of the composition of the sand after evaporation of the water and alcohol indicates no chemical or physical changes in the formation mix. A special jig allows an electrode to be placed in a fixed parallel position and then a disk to be set on top of the electrode. The wires of succeeding grids are preferably set at a slight angle to one another.

This pattern is repeated for succeeding disks and electrodes. In the resultant test sample, the electrodes are substantially parallel to each other but the protruding tabs of successive electrodes are rotated by a small angle relative to each other. When an electrode is placed on the top of a disk, formation sand is then sprinkled in to fill the holes in the grid pattern before the next disk is placed on top of the electrode. After the whole unit is assembled, a plastic sleeve is clamped around the moistened assembly which is then frozen in liquid nitrogen. Subsequent to removal of the sleeve, this frozen array is easily inserted into the combustion tube and formation sand is packed around the outside of the array to hold it firmly in place. The sheated wires are fed out through ceramic stand off insulators in an end plate. The wires are then routed through another high temperature, high pressure feedthrough in an end flange of the pressure vessel 14. The leads from the grids are connected to a patch panel for connection to a system control computer and an impedance analyzer.

Figure 3A:
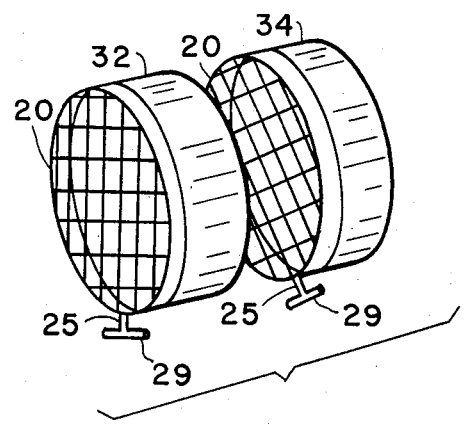
FIG. 3A illustrates an arrangement of a plurality of inventive electrodes with disks of a reconstituted core sample for use in a test apparatus.
Figure 3B:
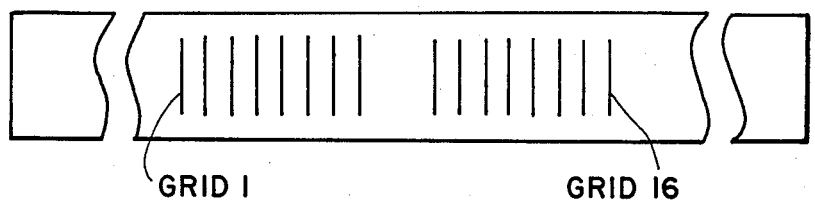
FIG. 3B shows an arrangement of sixteen grid electrodes in a test fixture in accordance with the invention.

FIG. 3A shows an exploded view of succession of core sample disks in combination with the inventive grid electrodes, wherein electrodes 20 are seen to be associated with core sample disks 32 and 34. As seen in the figure, tabs 25 and tubular sleeves 29 for the electrodes of the successive disks are rotated at a slight angle to one another. A schematic representation of one possible application of the spacing of the grid electrodes and core sample disks is shown at FIG. 3B, where sixteen grids are provided in two groups of eight, the grids within each group separated from one another by the disks and the two groups, in turn, separated from each other.

It is to be noted that the thermocouple wires 26 which are used to make electrical contact with the grid wires of electrodes of the various electrodes 20 are further usable for providing temperature measurement data, thus obtaining temperature distribution data within the combustion tube.

As is apparent from reference to FIG. 2, the inventive electrode provides a flow-through construction, permitting nondestructive passage of various phase fronts therethrough. Specifically, in the inventive structure, a front is not retarded by the electrode, and may pass therethrough without destroying the same. Moreover, the various other phases known to exist within a combustion tube are similarly not hindered by the electrode so that the constituted core sample within the combustion tube accurately simulates the actual structure found in the underground reservoir.

Earlier measurements of the electrical impedance of similar core samples have indicated that capacitance and conductance provide a sensitive measure for the changes of resistivity expected to occur with passage of thermal fronts and other phase fronts. A self-contained impedance measuring instrument may thus be connected to the electrodes in the test fixture, along with a computer to control the instrument. Preferably, the computer is used to control the test sequence, analyze the resulting data and to store the data for further analysis.

An actual application of the test fixture described above was to the study of in situ combustion processes. The laboratory procedure simulating in situ combustion includes application of heat (300°-400° C.) to one end of a combustion tube containing a reconstituted core sample and a plurality of the grid electrodes as hereinabove described. Air is blown through the tube and ignition of the core sample is started at the inlet side. A combustion zone propagates through the core sample within the tube and data are obtained for approximately 20-24 hours. With the inventive electrodes, data are provided for each electrode for the duration of the experiment.

Figure 4:
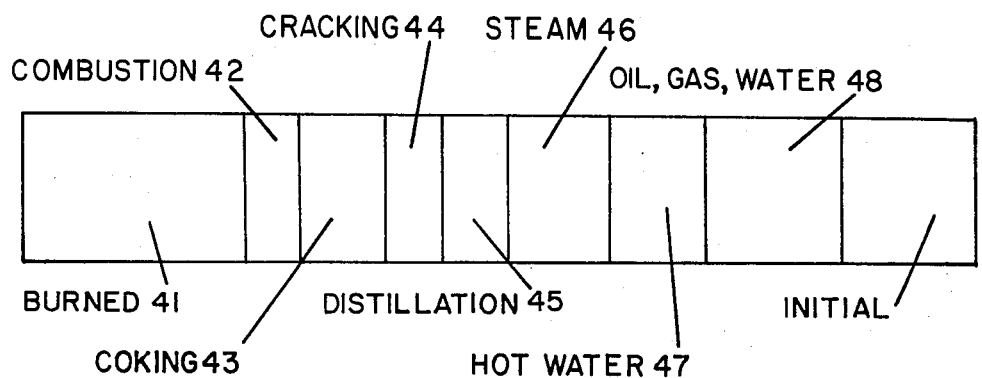
FIG. 4 describes the various zones in a fire flood experiment conducted in a test fixture of FIG. 1.

Test results obtained with the inventive structure indicate that when a fire front propagates down the tube eight distinct zones are formed. These zones are indicated in FIG. 4 and each is described below. In a zone 41 through which fire has passed, there is clean burned sand, with perhaps a very slight amount of moisture trapped from the injected air. The combustion front in zone 42 is normally quite thin and, of course, at the highest temperature. Directly preceding the combustion front is a coking zone 43 where the leftover residue from the stripped oil remains trapped in the formation. This coke acts as the fuel for the burning front. The next zone 44 contains the products from the cracking of the stripped off oil. Preceding the cracking zone is the distillation front 45. Steam formed from combustion and boiled off conate water passes from superheated to saturated steam in zone 46 before condensing to form a hot water front 47. At the leading edge of the water front the temperature is almost down to reservoir temperature. Oil, blowby gases and fine combustion ash are ahead of the water zone in a separate area 48 that is often large in extent. The various components to be found in each zone are given in Table 1:

TABLE 1

| Zone | Typical contents in addition to formation sand |
|---|---|
| Burned | Air |
| Combustion | Coke, Air, $CO_2$, CO, $H_2O$ |
| Coke | $O_2$, $CO_2$, CO, Steam |
| Cracking | $O_2$, $CO_2$, CO, Steam, Hydrocarbon (same as vapors) |
| Distillation | $O_2$, $CO_2$, CO, Steam, Hydrocarbon and Oil Residues |
| Steam | $O_2$, $CO_2$, CO, Steam, Hydrocarbons and Oil Residues |
| Water | $O_2$, $CO_2$, CO, $H_2O$ |
| Pre-Burn Front | Initial Formation Plus Above Gaseous Products |

By a comparison of the thermocouple, pressure and gas chromatograph records, it is possible to identify the different zones of the first flood as they pass through the electrodes. During the test, the parallel capacitance and resistivity between each set of electrodes is recorded at various frequencies. Typical values of the resistivity and capacitance in the zones of the fire flood are given in Table 2. These dynamic values measured between sets of electrodes are seen to change as the fire flood passes the electrodes. For specific formation deposits, the data may vary.

TABLE 2

TYPICAL VALUES OF RESISTIVITY AND CAPACITANCE IN THE ZONES OF FIRE FLOOD

| Zone | Frequency, Hz | Resistivity (ohm-m) | C (μfd) |
|---|---|---|---|
| Burned | 20 | 2.4064 + 4 | 7.231 |
|  | 1000 | 2.7525 + 3 | .2409 |
| Combustion | 20 | 4.3028 + 4 | 4.703 |
|  | 1000 | 4.3028 + 3 | .1646 |
| Coke | 20 | 3.441 + 4 | 5.459 |
|  | 1000 | 4.0806 + 3 | .1194 |
| Cracking | 20 | 1.1712 + 4 | 13.719 |
|  | 1000 | 2.791 + 3 | .387 |
| Distillation | 20 | 5.325 + 2 | 19.6 |
|  | 1000 | 3.7595 + 2 | .883 |
| Water Bank: |  |  |  |
| Live Steam | 20 | 4.0722 + 2 | 27.64 |
|  | 1000 | 2.8818 + 2 | 1.04 |
| Hot Water | 20 | 3.2543 + 2 | 20.23 |
|  | 1000 | 2.6327 + 2 | .413 |
| Oil, Water, Gas | 20 | 6.6303 + 2 | 38.09 |
|  | 1000 | 4.4741 + 2 | .466 |
| Initial | 20 | 7.5815 + 2 | 31.56 |
|  | 1000 | 5.0648 + 2 | .404 |

The changes in electrical properties between the cracking front and the distillation front are almost two decades in the lower frequencies and dwindle to a decade at the higher frequencies. Also, there is no sharp reduction in the resistivity ahead of the combustion front. The capacitance changes are not as large as the resistance changes as the fire front passes and indeed the capacitance increases as the electrolyte is removed from the formation. Preliminary examination of the capacitance data, however, indicates that capacitance variations may actually provide more information for uniquely identifying zones and frontal instabilities as they pass through a set of electrodes than do the resistivity data. An example is provided in the sequel.

When the electrodes are removed from the combustion tube, some changes are observed. Unlike prior art painted electrodes, however, the inventive structures maintain their electrical integrity. It was noted, however, that although the gold covering was stripped from the stainless steel, the electrodes nonetheless maintained their spacing and did not warp.

Figure 5:
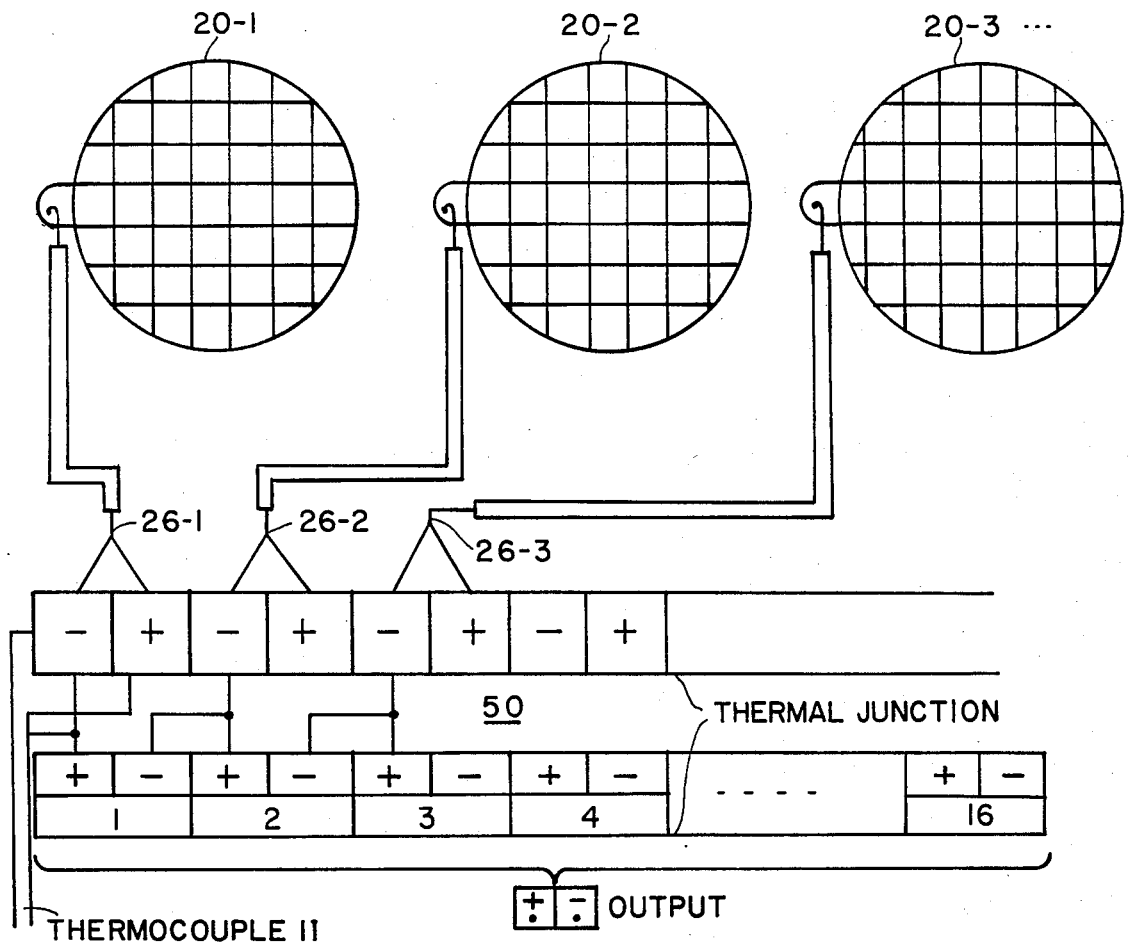
FIG. 5 illustrates an electrical connection for a plurality of test electrodes used in the inventive test equipment.

Referring now to FIG. 5, there is shown schematically an electrical configuration of the test electrodes connected in accordance with one aspect of the invention, wherein the thermocouple wires are connected to provide temperature data therefor. Each of the flow-through grid electrodes is labelled as 20-1, 20-2, etc. The appropriate thermocouple wires emanating therefrom are similarly labelled at 26-1, 26-2, 26-3, etc. The individual thermocouples formed for each of the electrodes are connected in a series configuration, as shown generally at 50, to provide the desired temperature distribution data within the test fixture.

The present invention is also applicable to detection of passage of immiscible fluids through porous media. An application of the inventive structure to detection and measurement of frontal instabilities, such as fingering which occurs in frontal displacement for such fluids, is illustrated with reference to FIGS. 6A–6F. In each of these figures, there are shown two grid electrodes as hereinabove described. These electrodes are labelled as 20a, 20b, respectively. A phase front 60 is shown in the figures moving in the direction indicated by arrow 62 at FIG. 6A.

Various instabilities may be associated with phase front 60, as illustrated by fingering of the front at 64.

The resistivity or capacitance of the medium between electrodes 20a and 20b is measured substantially continuously (or at very frequent intervals) to determine progress of the phase front and its associated fingers.

Figure 6A:
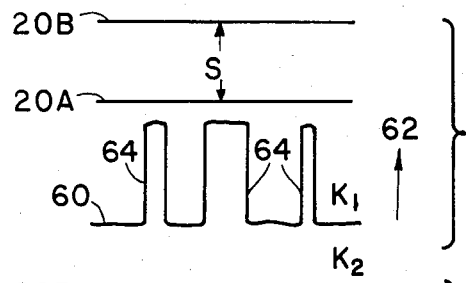
FIGS. 6A, 6B, 6C, 6D, 6E and 6F illustrate passage of a front, along with frontal instabilities, through a disk of core material between two test electrodes.
Figure 6B:
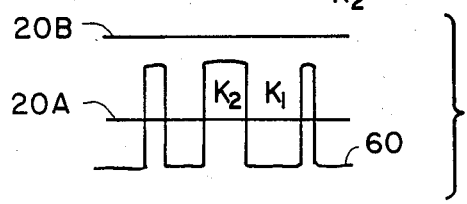
Figure 6C:
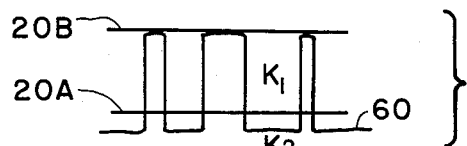
Figure 6D:
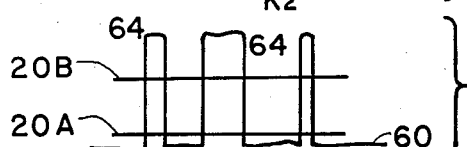
Figure 6E:
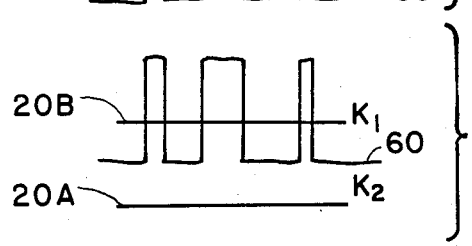

In the following description, it is assumed that the dielectric permittivity of the medium being displaced is $K_1$, and that the permittivity of the displacing material, behind the phase front, is $K_2$. Thus, for a situation as depicted in FIG. 6A, the capacitance measured between electrodes 20a and 20b is given by equation 1:

$$C_a = \frac{K_1 A}{4\pi s} \quad (1)$$

where A is the cross-sectional area of the material between electrodes 20a and 20b and s is the separation between the electrodes. It is noted that as the phase front continues its motion in the direction of arrow 62, there will initially be an intersection of the fingers resultant from frontal instability with electrode 20a as shown in FIG. 6B. Inasmuch as the fingers represent material having dielectric permittivity $K_2$, the capacitance measured between electrodes 20a and 20b will begin to change once the fingers penetrate the interelectrode gap. The change in the capacitance will continue until the fingers reach and pass the top electrode 20b as shown in FIG. 6C, and will remain constant until the displacement front 60 passes the electrode 20a as shown in FIG. 6D. The measured capacitance will then again change as the phase front 60 passes between the electrodes, as shown in FIG. 6E, until passage of the front through the top electrode 20b, as shown at FIG. 6F.

Figure 6F:
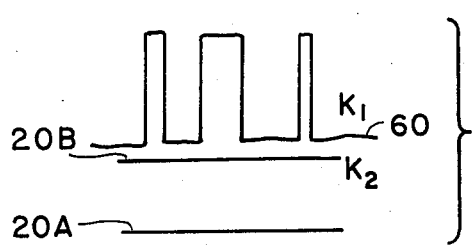

As is apparent from consideration of the situation in FIG. 6F, the capacitance measured between electrodes 20a and 20b is given by equation 2:

$$C_b = \frac{K_2 A}{4\pi s} \quad (2)$$

It is noted that for the situations illustrated at FIGS. 6C and 6D, there are effectively two parallel capacitances between the two electrodes. A first capacitance is formed of the material having dielectric constant $K_1$, and is given by equation 3:

$$C_1 = \frac{(1 - \Delta) A K_1}{4\pi s} \quad (3)$$

where $\Delta$ represents the fraction of the cross-sectional area covered by the fingers 64. A second capacitance, in parallel with the first capacitance, is due to the fingers themselves and is represented by equation 4:

$$C_2 = \frac{\Delta A K_2}{4\pi s} \quad (4)$$

Thus, the effective capacitance measured between electrodes 20a and 20b during the situation illustrated by FIGS. 6C and 6D is given by equation 5:

$$C_e = C_1 + C_2 = \frac{A}{4\Delta s}[K_1 + \Delta(K_2 K_1)] \quad (5)$$

Equation 5, in conjunction with equations 1 and 2, may be solved for $\Delta$ as shown at equation 6:

$$\Delta = \frac{\frac{4\pi s C_e}{A} - K_1}{K_2 - K_1} = \frac{\frac{4\pi s C_e}{A} - \frac{4\pi s C_a}{A}}{\frac{4\pi s C_b}{A} - \frac{4\pi s C_a}{A}} = \frac{C_e - C_a}{C_b - C_a} \quad (6)$$

As previously described, $C_a$ is a steady capacitance measured between the electrodes, $C_b$ is similarly a steady capacitance measured between the electrodes, and $C_e$ is a steady value of capacitance measured between measurements of $C_a$ and $C_b$ but separated therefrom by periods of varying capacitances, illustrated by the situations at FIGS. 6D and 6E. Thus, with the aid of the inventive electrodes and the foregoing analysis it is possible to determine the fractional area covered by fingering of a moving phase front.

It should also be noted that a similar analysis may be carried out for resistivity measurements, and that in that situation $\Delta$ is given by equation 7:

$$\Delta = (R_a R_b - R_b R_e)/(R_a R_e - R_b R_e) = ((R_a/R_e) - 1)/((R_a/R_b) - 1).$$

where $R_a$ represents the resistance measured between electrodes 20a and 20b for the situation in FIG. 6A, $R_b$ represents the resistance measured between the electrodes for the situation depicted by FIG. 6F, and $R_e$ represents the resistance measured for the situation depicted in FIGS. 6C and 6D.

It is further noted that other characteristics of the frontal instabilities, illustrated by fingers 64, may be measured with the aid of the present structure. For example, the velocity of the fingers may be determined as the ratio of the spacing between the electrodes to the time between the first stable capacitance (or resistance)

measurement for the situation of FIG. 6A and the second stable measurement of the electrical parameter for the situation of FIGS. 6C and 6D. Further, the length of the fingers may be determined by equation 8:

$$l_f = s + v_f \Delta t_d \tag{8}$$

where $v_f$ represents the finger velocity previously described and $\Delta t_d$ represents the time of constant capacitance or resistance represented by the situation in FIGS. 6C and 6D.

Still further, the velocity of the main bank of the phase front is described by equation 9:

$$V_b = s/\Delta t_e \tag{9}$$

where $\Delta t_e$ represents the time during which the resistance or capacitance is changing in accordance with the situation shown in FIG. 6E.

Other parameters descriptive of the moving phase front may also be measured with the aid of the inventive electrode.

In summary, numerous benefits have been described which result from employing the concepts of the present invention. For example, accurate laboratory representation of an in situ enhanced oil recovery process may be had, data being available before, during and after passage of any of a plurality of zones, as shown in FIG. 4, which make up the front, for example. Additionally, accurate computation of various parameters descriptive of frontal instabilities associated with movement of the phase front is enabled by the invention.

These data and parameters may be used in conjunction with electromagnetic geological prospecting techniques to obtain accurate position information for phase fronts, frontal instabilities, and the like, progressing through a reservoir formation during enhanced oil recovery operation.

The foregoing description of the preferred embodiment of the invention has been presented for purposes of illustration and description. It is not intended to be exhaustive or to limit the invention to the precise form disclosed. Obvious modifications or variations are possible in light of the above teachings. The disclosed embodiment was chosen and described to provide the best illustration of the principles of the invention and its practical application, thereby to enable one of ordinary skill in the art to utilize the invention in various embodiments and with various modifications as are suited to the particular use contemplated. It is intended that the scope of the invention be defined by the claims appended hereto.

We claim:

1. Apparatus for obtaining dynamic electrical parameter data for a core of material, said apparatus comprising:
   a plurality of test electrodes, each electrode including structural means for permitting nondestructive passage of a phase front therethrough;
   a plurality of reconstituted core material samples; and
   housing means defining a combustion tube for holding an alternating pattern of said core material samples and said test electrodes;
   the electrical impedance between two of said test electrodes providing accurate dynamic characteristics of said core material throughout the passage of the phase front.

2. Apparatus as recited in claim 1 wherein each of said test electrodes comprises a grid structure of electrically conductive material.

3. Apparatus as recited in claim 2 wherein said housing comprises a test fixture having an outer surface and a plurality of heaters disposed along said outer surface, said heaters dividing said combustion tube into a plurality of zones.

4. Apparatus as recited in claim 2 further comprising an outer peripheral support surrounding said grid structure and tab means extending outwardly therefrom for providing electrical connection thereto.

5. Apparatus as recited in claim 2 wherein said grid structure comprises a rectangular grid pattern of wires.

6. Apparatus as recited in claim 5 wherein said wires are approximately 0.5 mm in diameter on a 6 mm grid spacing.

7. Apparatus as recited in claim 2 further comprising connecting means for providing external connections to each of said test electrodes, said connecting means comprising sheathed stainless steel wires, whereby the impedance between two test electrodes is measured across two connecting means.

8. In a method for enhanced oil recovery incorporating a fire flood, the improvement comprising the steps of:
   reconstituting a sample of geological core material;
   combining the reconstituted sample with a plurality of flow-through electrodes in a test fixture;
   introducing a front in the test fixture;
   obtaining electrical characteristics of the reconstituted core sample in the test fixture between two electrodes before, during and after passage of the front through the fixture.

9. The method recited in claim 8 comprising the further step of determining the area of fingers of said front between two of said electrodes as a function of the electrical characteristics obtained for the core sample.

10. The method recited in claim 9 wherein said step of determining includes the steps of:
    measuring a capacitance between said two electrodes before introduction of the fingers therebetween, during the presence of the fingers, and after passage of the front therethrough, and
    performing a numerical computation on the measured capacitances to determine the area of the fingers.

11. A method as recited in claim 8 wherein the step of initiating a front comprises the step of igniting the material.

* * * * *